(12) United States Patent
Lee et al.

(10) Patent No.: US 7,429,567 B2
(45) Date of Patent: Sep. 30, 2008

(54) SUSTAINED DELIVERY OF PDGF USING SELF-ASSEMBLING PEPTIDE NANOFIBERS

(75) Inventors: Richard T. Lee, Weston, MA (US); Patrick Hsieh, Cambridge, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 11/320,468

(22) Filed: Dec. 29, 2005

(65) Prior Publication Data

US 2006/0148703 A1 Jul. 6, 2006

Related U.S. Application Data

(60) Provisional application No. 60/702,318, filed on Jul. 26, 2005, provisional application No. 60/640,998, filed on Jan. 4, 2005.

(51) Int. Cl.
*A61K 38/18* (2006.01)
(52) U.S. Cl. ............................ 514/21; 514/8; 514/12; 530/409
(58) Field of Classification Search ................ None
See application file for complete search history.

(56) References Cited

U.S. PATENT DOCUMENTS

| | | | |
|---|---|---|---|
| 5,670,483 | A | 9/1997 | Zhang et al. |
| 5,955,343 | A | 9/1999 | Holmes et al. |
| 6,086,866 | A * | 7/2000 | Kouri ........................ 424/85.1 |
| 6,548,630 | B1 | 4/2003 | Zhang et al. |
| 2002/0160471 | A1 | 10/2002 | Kisiday et al. |
| 2003/0139333 | A1 * | 7/2003 | Pawliuk et al. ................ 514/12 |
| 2004/0105839 | A1 | 6/2004 | Park |
| 2004/0253679 | A1 * | 12/2004 | Epstein et al. ............. 435/69.1 |

FOREIGN PATENT DOCUMENTS

WO WO 03/096972 A2 * 11/2003
WO WO 2004/045531 A 2 * 6/2004

OTHER PUBLICATIONS

Hsieh et al. Controlled Delivery of PDGF-BB, an Endothelial-Derived Cardiomyocyte Survival Factor . . . Circulation. Oct. 25, 2006, vol. 112, No. 17, Supplement II, pp. II-J and II-K.*
Clarke, et al., "Transformation of NIH 3T3 Cells by a Human *c-sis* cDNA Clone," *Nature* 308:464 (1984).
Gazit, et al., "Expression of the Normal Human *sis*/PDGF-2 Coding Sequence Induces Cellular Transformation,"*Cell* 39:89 (1984).
Davis, et al., "Injectable Self-Assembling Peptide Nanofibers Create Intramyocardial Microenvironments for Endothelial Cells," *Circulation* 111:442-450 (2005).
Smits, et al., "Expression of Platelet-Derived Growth Factor and Its Receptors in Proliferative Disorders of Fibroblastic Origin," *Am. J. Pathol.* 140:639 (1992).
Ferns, et al., "Inhibition of Neointimal Smooth Muscle Accumulation After Angioplasty by an Antibody to PDGF," *Science* 253:1129-1132 (1991).
Rutherford et al., "Substantial Inhibition of Neo-Intimal Response to Ballon Injury in the Rat Carotid Artery Using a Combination of Antibodies to Platelet-Derived Growth Factor-BB and Basic Fibroblast Growth Factor," *Atherosclerosis* 130:45-51 (1997).
Jawien et al., "Platelet-Derived Growth Factor Promotes Smooth Muscle Migration and Intimal Thickening in a Rat Model of Ballon Angioplasty," *J. Clin. Invest.* 89:507-511 (1992).
Deuel, et al., "Chemotaxis of Monocytes and Neutrophils to Platelet-Derived Growth Factor," *J. Clin. Invest.* 69:1046-1049 (1981).
Siegbhan, et al., "Differential Effects of the Various Isoforms of Platelet-Derived Growth Factor on Chemotaxis of Fibroblasts, Monocytes, and Granulocytes," *J. Clin. Invest.* 85:916-920 (1990).
Smits, et al., "Neurotropic Activity of Platelet-Derived Growth Factor (PDGF): Rat Neuronal Cells Possess Functional PDGF β-Type Receptors and Respond to PDGF," *Proc. Natl. Acad. Sci. USA.* 88:8159-8163 (1991).
Yeh, et al., "PDGF: A-Chain Gene is Expressed by Mammalian Neurons During Development and in Maturity," *Cell* 64:209-216 (1991).
Robson, et al., "Platelet-Derived Growth Factor BB for the Treatment of Chronic Pressure Ulcers," *Lancet* 339:23-25 (1992).
Narmoneva, et al., "Endothelial Cells Promote Cardiac Myocyte Survival and Spatial Reorganization: Implications for Cardiac Regeneration," *Circulation* 110:962-968 (2004).
Kuramochi, et al., "Cardiac Endothelial Cells Regulate Reactive Oxygen Species-Induced Cardiomyocyte Apoptosis Through Neuregulin-1β/erbB4 Signaling," *J. Biol. Chem.* 279:51141-51147 (2004).
International Search Report for PCT/US05/46768.
"Written Opinion of the International Searching Authority for PCT/US05/46768".

* cited by examiner

*Primary Examiner*—Jeffrey E Russel
(74) *Attorney, Agent, or Firm*—Michael A. Sanzo; Law Office of Michael A. Sanzo, LLC

(57) ABSTRACT

The present invention is directed to a therapeutic composition in which human PDGF is bound directly to peptides that self assemble into a biologically compatible gel. When implanted in a patient's body, the composition provides for the slow, sustained release of PDGF. The composition will be especially useful in treating patients who have undergone a myocardial infarction.

20 Claims, 1 Drawing Sheet

SUSTAINED DELIVERY OF PDGF USING SELF-ASSEMBLING PEPTIDE NANOFIBERS

CROSS REFERENCE TO RELATED APPLICATIONS

The present application claims the benefit of, and priority to, U.S. provisional applications 60/640,998, filed Jan. 4, 2005, and 60/702,318 filed on Jul. 26, 2005.

FIELD OF THE INVENTION

The present invention is directed to a therapeutic membrane composition formed by self-assembling peptides and platelet derived growth factor (PDGF). The membrane/PDGF complex may be implanted or injected into the heart of a patient to provide for the long term release of free PDGF.

BACKGROUND OF THE INVENTION

Certain peptides are capable of self assembly when incubated in the presence of a low concentration of monovalent metal cation (U.S. Pat. No. 5,670,483; 6,548,630). Assembly results in the formation of a gel-like membrane that is non-toxic, non-immunogenic and relatively stable to proteases. Once formed, membranes are stable in serum, aqueous solutions and cell culture medium. They can be made under sterile conditions, are capable of supporting the growth of cells and are slowly digested when implanted in an animal's body. These characteristics make the membranes well suited as devices for the delivery of therapeutic agents. Among the most promising of such agents is platelet-derived growth factor (PDGF).

PDGF is a mitogen for connective tissue cells, fibroblasts and smooth muscle cells. It has been implicated as contributing to malignant transformation (Clarke, et al., *Nature* 308: 464 (1984); Gazit, et al., *Cell* 39:89 (1984); Beckmann, et al., *Science* 241:1346 (1998); Smits, et al., *Am. J. Pathol.* 140:639 (1992)); and, by promoting the growth of endothelial cells, may contribute to the angiogenesis needed to sustain tumor growth. There is also evidence that PDGF contributes to the restenosis that often occurs after angioplasty (Ferns, et al., *Science* 253:1129-1132 (1991); Rutherford et al., *Atherosclerosis* 130:45-51 (1997); Jawien et al. *J. Clin. Invest.* 89:507-511 (1992)) and to the development of fibrotic lesions in several different organs (*Experimental Pharmacology, Peptide Growth Factors and Their Receptors*, Sporn & Roberts, eds., pp. 173-262, Springer, Heidelberg).

From a therapeutic perspective, PDGF appears to play a role in promoting the growth of neuronal tissue and in wound healing (Deuel, et al., *J. Clin. Invest.* 69:1046-1049 (1981); Siegbhan, et. al., *J. Clin. Invest.* 85:916-920 (1990); Smits, et al., *Proc. Natl. Acad. Sci. USA.* 88:8159-8163 (1991); Yeh, et al., *Cell* 64:209-216 (1991); Robson, et al., *Lancet* 339:23-25 (1992)). There are also indications that PDGF may be used to help preserve cardiac function in patients following a myocardial infarction.

SUMMARY OF THE INVENTION

One problem with using membranes formed from self-assembling peptides for drug delivery is that compounds simply enmeshed in the peptide matrix, tend to be rapidly lost after implantation due to the high permeability of membranes. The present invention is based upon the discovery that PDGF, and particularly the B chain of PDGF, binds naturally to self-assembling peptides. This allows biological membranes to be formed that have immobilized PDGF directly attached and which can be implanted in vivo without the PDGF being rapidly washed away. Using a rat model of myocardial injury, membranes with bound PDGF can be locally injected into injured myocardium and are retained at the delivery site for at least 14 days after coronary artery ligation. As a result, cardiomyocyte death is decreased and myocardial systolic function is preserved. Thus, membranes with bound PDGF provide an effective method for preventing heart failure after myocardial infarction.

In its first aspect, the invention is directed to a biologically compatible peptide membrane made of self-assembling peptides. The term "biologically compatible" indicates that the membranes are non-toxic and can be safely implanted in a patient. The self-assembling peptides should be 12-200 amino acids in length and have alternating hydrophobic and hydrophilic amino acids. In addition, the peptides should be complementary (i.e., they should be able to form ionic or hydrogen bonds with one another) and structurally compatible (i.e., the bound peptide chains should maintain a distance from one another that does not vary by more than about three angstroms throughout their length). In general, at least 0.1 %, more preferably 0.5% - 10%, and still more preferably 1-10% of the peptides that assemble into the membrane should be bound directly to PDGF. The term "bound directly" as used herein means that there is no linker or other molecule interspersed between PDGF and peptide. The term also requires that there be a physical interaction of some type between the PDGF and peptide (e.g., an ionic bond, hydrophobic interaction etc.) that prevents the PDGF from diffusing away from peptide in aqueous medium as it would do if simply enmeshed within the gel matrix.

In preferred embodiments, the self-assembling peptides used in membranes are between 12 and 24 amino acids in length, have PDGF attached to about 4-8% of the peptides, and are homogeneous. The term "homogeneous" as used in this context indicates that all of the peptides forming the biologically compatible membrane are identical. The term "heterogeneous" refers to non-identical peptides that are used to form membranes. Specific peptides that may be used in the membranes described above include:

| | |
|---|---|
| AKAKAEAEAKAKAEAE, | (SEQ ID NO:1); |
| AKAEAKAEAKAEAKAE, | (SEQ ID NO:2); |
| EAKAEAKAEAKAEAKA, | (SEQ ID NO:3); |
| KAEAKAEAKAEAKAEA, | (SEQ ID NO:4); |
| AEAKAEAKAEAKAEAK, | (SEQ ID NO:5); |
| ADADARARADADARAR, | (SEQ ID NO:6); |
| ARADARADARADARAD, | (SEQ ID NO:7); |
| DARADARADARADARA, | (SEQ ID NO:8); |
| RADARADARADARADA, | (SEQ ID NO:9); |
| ADARADARADARADAR, | (SEQ ID NO:10); |
| ARADAKAEARADAKAE, | (SEQ ID NO:11); |
| AKAEARADAKAEARAD, | (SEQ ID NO:12); |
| ARAKADAEARAKADAE, | (SEQ ID NO:13); |
| AKARAEADAKARADAE, | (SEQ ID NO:14); |

```
                       -continued
AQAQAQAQAQAQAQAQ,           (SEQ ID NO:15);

VQVQVQVQVQVQVQVQ,           (SEQ ID NO:16);

YQYQYQYQYQYQYQYQ,           (SEQ ID NO:17);

HQHQHQHQHQHQHQHQ,           (SEQ ID NO:18);

ANANANANANANANAN,           (SEQ ID NO:19);

VNVNVNVNVNVNVNVN,           (SEQ ID NO:20);

YNYNYNYNYNYNYNYN,           (SEQ ID NO:21);

HNHNHNHNHNHNHNHN,           (SEQ ID NO:22);

ANAQANAQANAQANAQ,           (SEQ ID NO:23);

AQANAQANAQANAQAN,           (SEQ ID NO:24);

VNVQVNVQVNVQVNVQ,           (SEQ ID NO:25);

VQVNVQVNVQVNVQVN,           (SEQ ID NO:26);

YNYQYNYQYNYQYNYQ,           (SEQ ID NO:27);

YQYNYQYNYQYNYQYN,           (SEQ ID NO:28);

HNHQHNHQHNHQHNHQ,           (SEQ ID NO:29);

HQHNHQHNHQHNHQHN,           (SEQ ID NO:30);

AKAQADAKAQADAKAQAD,         (SEQ ID NO:31);

VKVQVDVKVQVDVKVQVD,         (SEQ ID NO:32);

YKYQYDYKYQYDYKYQYD,         (SEQ ID NO:33);

HKHQHDHKHQHDHKHQHD,         (SEQ ID NO:34);

RARADADARARADADA,           (SEQ ID NO:35);

RADARGDARADARGDA,           (SEQ ID NO:36);

RAEARAEARAEARAEA,           (SEQ ID NO:37);

KADAKADAKADAKADA,           (SEQ ID NO:38);

AEAEAHAHAEAEAHAH,           (SEQ ID NO:39);

FEFEFKFKFEFEFKFK,           (SEQ ID NO:40);

LELELKLKLELELKLK,           (SEQ ID NO:41);

AEAEAKAKAEAEAKAK,           (SEQ ID NO:42);

AEAEAEAEAKAK,               (SEQ ID NO:43);

KAKAKAKAKAEAEAEA,           (SEQ ID NO:44);

AEAEAEAEAKAKAKAK,           (SEQ ID NO:45);

RARARARADADADADA,           (SEQ ID NO:46);

ADADADADARARARAR,           (SEQ ID NO:47);

DADADADARARARARA,           (SEQ ID NO:48);

HEHEHKHKHEHEHKHK,           (SEQ ID NO:49);

VEVEVEVEVEVEVEVEVE,         (SEQ ID NO:50);
and

RFRFRFRFRFRFRFRFRF,         (SEQ ID NO:51).
```

It should be recognized that each of the peptides listed above includes a repeating sequence and that additional repeats can be included to extend the length of the peptides without destroying their ability to self-assemble. For example, the peptide AKAKAEAEAK AKAEAE (SEQ ID NO:1) has the repeating sequence AKAKAEAE (SEQ ID NO:52) and can be expressed as (AKAKAEAE)$_n$ (SEQ ID NO:52) where n=2. Longer peptides capable of self assembly can be made by increasing n with the caveat that the total number of amino acids in the final peptide cannot exceed 200. Preferred peptides are those having the following repeating structures: (RARADADA)$_n$ (SEQ ID NO:53) (ARARADAD)$_n$ (SEQ ID NO:89), (RADARADA)$_n$ (SEQ ID NO:54) and (AEAEAKAK)$_n$ (SEQ ID NO:55) in which n=2-10. Preferably, n=2-4 and more preferably, n=2.

Other peptides expressed in this manner and useful in the invention are: (AKAKAEAE)$_n$ (SEQ ID NO:52) where n=2-25; (KAEA)$_n$ (SEQ ID NO:56) where n=3-50; (EAKA)$_n$ (SEQ ID NO:57) where n=3-50; (KAEA)$_n$ (SEQ ID NO:58) where n=3-50; (AEAK)$_n$ (SEQ ID NO:59) where n=3-50; (ADADARAR)$_n$ (SEQ ID NO:60) where n=2-25; (ARAD)$_n$ (SEQ ID NO:61) where n=3-50; (DARA)$_n$ (SEQ ID NO:62) where n=3-50; (RADA)$_n$ (SEQ ID NO:63) where n=3-50; (ADAR)$_n$ (SEQ ID NO:64) where n=3-50; (ARADAKAE)$_n$ (SEQ ID NO:65) where n=2-25; (AKAEARAD)$_n$ (SEQ ID NO:66) where n=2-25; (ARAKADAE)$_n$ (SEQ ID NO:67) where n=2-25; (KARAEADA)$_n$ (SEQ ID NO:68) where n=2-25; (AQ)$_n$ where n=6-100; (VQ)$_n$ where n=6-100; (YQ)$_n$ where n=6-100; (HQ)$_n$ where n=6-100; (AN)$_n$ where n=6-100; (VN)$_n$ where n=6-100; (YN)$_n$ where n=6-100; (HN)$_n$ where n=6-100; (ANAQ)$_n$ (SEQ ID NO:69) where n=3-50; (AQAN)$_n$ (SEQ ID NO:70) where n=3-50; (VNVQ)$_n$ (SEQ ID NO:71) where n=3-50; (VQVN)$_n$ (SEQ ID NO:72) where n=3-50; (YNYQ)$_n$ (SEQ ID NO:73) where n=3-50; (YQYN)$_n$ (SEQ ID NO:74) where n=3-50; (HNHQ)$_n$ (SEQ ID NO:75) where n=3-50; (HQHN)$_n$ (SEQ ID NO:76) where n=3-50; (AKAQAD)$_n$ (SEQ ID NO:77) where n=2-33; (VKVQVD)$_n$ (SEQ ID NO:78) where n=2-33; (YKYQYD)$_n$ (SEQ ID NO:79) where n=2-33; (HKHQHD)$_n$ (SEQ ID NO:80) where n=2-33; (RARADADA)$_n$ (SEQ ID NO:53) where n=2-25; (RADARGDA)$_n$ (SEQ ID NO:81) where n=2-25; (RAEA)$_n$ (SEQ ID NO:82) where n=3-50; (KADA)$_n$ (SEQ ID NO:83) where n=3-50; (AEAEAHAH)$_n$ (SEQ ID NO:84) where n=2-25; (FEFEFKFK)$_n$ (SEQ ID NO:85) where n=2-25; (LELELKLK)$_n$ (SEQ ID NO:86) where n=2-25; (AEAEAKAK)$_n$ (SEQ ID NO:55) where n=2-25; (AEAEAEAEAKAK)$_n$ (SEQ ID NO:87) where n=1-16; (KAKAKAEAEAEAEA)$_n$ (SEQ ID NO:44) where n=1-12; (AEAEAEAEAKAKAKAK)$_n$ (SEQ ID NO:45) where n=1-12; (RARARARADADADADA)$_n$ (SEQ ID NO:46) where n=1-12; (ADADADADARARARAR)$_n$ (SEQ ID NO:47) where n=1-12; (DADADADARARARARA)$_n$ (SEQ ID NO:48) where n=1-12; (HEHEHKHK)$_n$ (SEQ ID NO:88) where n=2-25; (VE)$_n$ where n=6-100; and (RF)$_n$ where n=6-100.

Membranes can be formed from the self-assembling peptides and then administered to a patient. Alternatively, the peptides and PDGF can be incorporated into an injectable pharmaceutical composition at a concentration of monovalent cation that is too low to induce membrane formation. This can then be administered to induce membrane formation in vivo. The invention encompasses the pharmaceutical compositions containing the PDGF and peptides as described above.

The invention also includes methods of treating patients using the membranes or pharmaceutical compositions described herein. Patients can be treated for any condition in which PDGF has been found to be useful and where implantation is appropriate. For example, membranes may be used to deliver PDGF at wound sites, at joints in which there is damage to a ligament, tendon or cartilage or at sites where neurons have been damaged. The most preferred use is in the treatment of patients that have had a myocardial infarction. In this case, the membrane should be injected directly into the myocardium as soon after the myocardial infarction as possible. The total amount of PDGF delivered will be determined on a case by case basis but, in general, should be between about 1 ng and 500 μg and, preferably between 10 ng and 100 μg.

In another aspect, the invention includes methods of making the biologically compatible membranes described above. This is accomplished by combining the self-assembling peptides in an aqueous medium containing sufficient monovalent metal cation to promote self assembly. Preferably, an aqueous solution containing a salt of the metal cation is formed first and peptides are then added to a final concentration of at least 1 mg/ml and preferably, at least 10 mg/ml. The concentration of monovalent metal cation can vary considerably but, in general, should be at least 5 mM. The upper limit for the cation is at least 3 M but assembly of peptides may occur at concentrations as high as 5 M. Preferred cations include lithium, sodium and potassium. These may be provided as salts in conjunction with essentially any pharmaceutically acceptable anion, including chloride, acetate and phosphate. The use of divalent cations should be avoided as these appear to interfere with peptide assembly. Similarly, concentrations of detergent, such as sodium dodecyl sulfate (SDS) of 0.1% or higher, should generally be avoided.

PDGF may be combined with the peptides either prior to, or after, self assembly. In general, sufficient PDGF should be added so that 0.1-10% of the peptides in the final assembled membrane have PDGF attached. However, an upper limit on the percentage of peptides that can be occupied has not yet been determined and, if desired, more than 10% (e.g., 15%, 25%) can be bound. It should be recognized that these percentages express the relative amount of PDGF molecules to peptides and do not necessarily mean that the PDGF is homogeneously distributed throughout the membrane. For example, the phrase "10% of peptides are bound to PDGF" means that, on average, one out of every 10 peptides are bound based on a knowledge of the number of PDGF molecules and the number of peptides present. Certain peptides may have more than one PDGF attached and others may have none. When membranes are formed prior to the attachment of peptides, the distribution of PDGF will tend to be less homogeneous than when peptides are bound prior to assembly. However, the non-homogeneous distribution should not affect the ability of the membranes to effectively deliver the PDGF after implantation.

DESCRIPTION OF THE INVENTION

Figure 1:
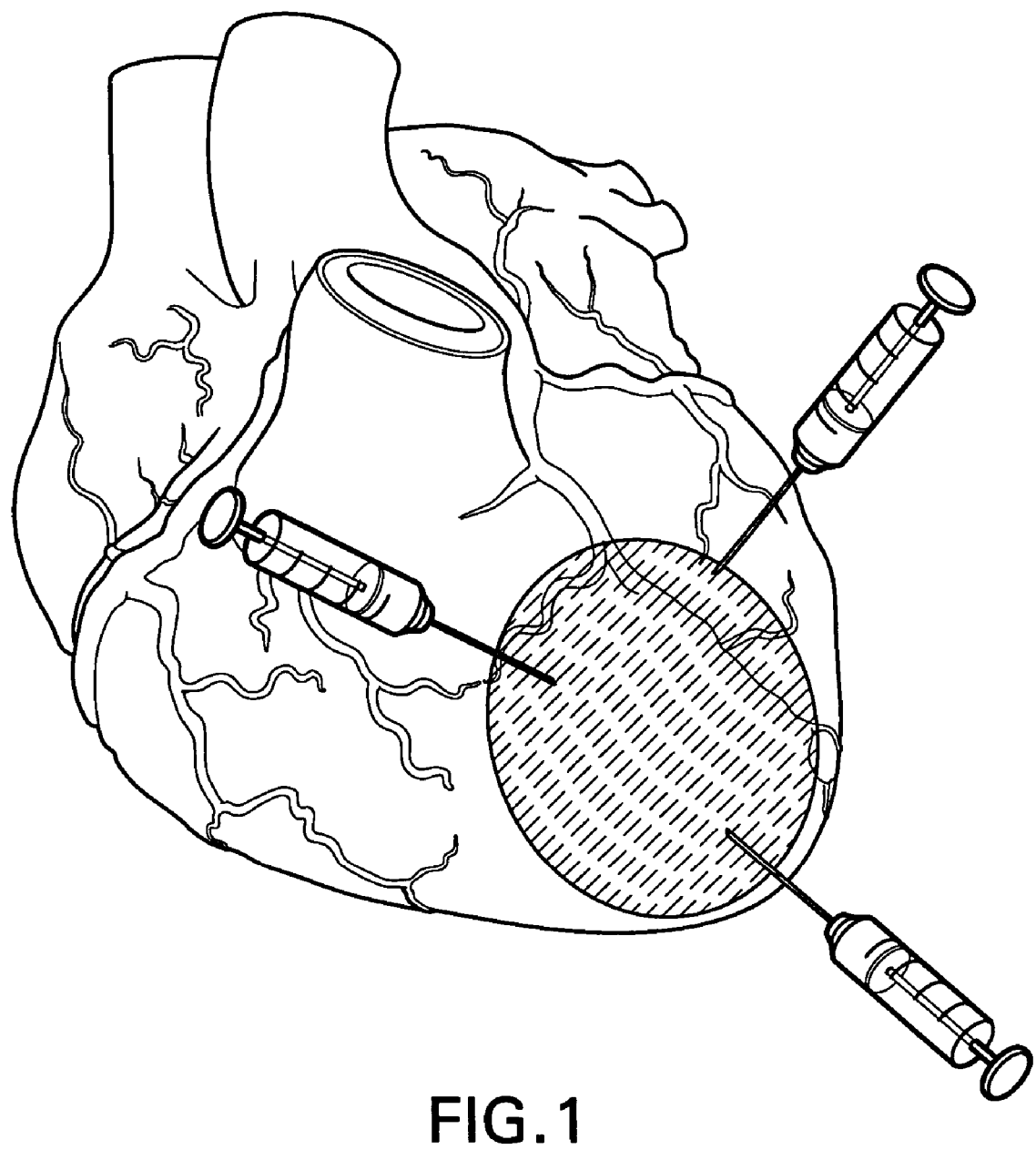
FIG. 1: Targeted delivery of PDGF-B with self-assembling peptide nanofibers into infarcted myocardium. Rat model of experimental myocardial infarction (MI) with peptide nanofiber (NF) injection. The peptide NF forms a gel-like structure after sonication and becomes consolidated after myocardial injection. The left coronary artery is permanently ligated, followed with 80 ul peptide NF injection in the border zones via 3 different directions.

The present invention is based upon the discovery that, in aqueous medium, PDGF-B spontaneously attaches to the self-assembling peptides described herein and is ultimately bound to the gel-like membranes that they form. It should be recognized that the term "membrane" in this context refers to a three dimensional solid hydrogel structure. For this reason, it may also be properly referred to as a "microenvironment."

The self-assembling peptides have been described in U.S. Pat. Nos. 5,670,483 and 6,548,630, both of which are hereby incorporated by reference. Essentially the same procedures described therein for making and using the peptides apply to the present invention. However, it has been found that PDGF can be non-covalently bound to the membranes formed by the self-assembling peptides by simply combining the membrane (or peptides) and PDGF in aqueous medium (e.g., water, saline or a buffer containing the components needed for the self assembly of peptides). It appears that, on average, at least 10% of the peptides within membranes can be bound to PDGF (i.e., 1 PDGF molecule bound for every 10 peptides) but an upper limit has not yet been determined and it may be possible to bind much larger amounts, e.g., 20%, 40%, 80% or more.

Description of Peptides

The peptides used for self assembly should be at least 12 residues in length and contain alternating hydrophobic and hydrophilic amino acids. Peptides longer than about 200 amino acids tend to present problems with respect to solubility and membrane stability and should therefore be avoided. Ideally, peptides should be about 12-24 amino acids in length.

The self-assembling peptides must be complementary. This means that the amino acids on one peptide must be capable of forming ionic bonds or hydrogen bonds with the amino acids on another peptide. Ionic bonds would form between acidic and basic amino acid side chains. The hydrophilic basic amino acids include Lys, Arg, His, and Orn. The hydrophilic acidic amino acids are Glu and Asp. Ionic bonds would form between an acidic residue on one peptide and a basic residue on another. Amino acids that form hydrogen bonds are Asn and Gln. Hydrophobic amino acids that may be incorporated into peptides include Ala, Val, Ile, Met, Phe, Tyr, Trp, Ser, Thr, and Gly.

Self-assembling peptides must also be "structurally compatible." This means that they must maintain an essentially constant distance between one another when they bind. Interpeptide distance can be calculated for each ionized or hydrogen bonding pair by taking the sum of the number of unbranched atoms on the side-chains of each amino acid in the pair. For example, lysine has five and glutamic acid has four unbranched atoms on their side chains. An interaction between these two residues on different peptides would result in an interpeptide distance of nine atoms. In a peptide containing only repeating units of EAK, all of the ion pairs would involve lysine and glutamate and therefore a constant interpeptide distance would be maintained. Thus, these peptides would be structurally complementary. Peptides in which the variation in interpeptide distance varies by more than one atom (about 3-4 angstroms) will not form gels properly. For example, if two bound peptides have ion pairs with a nine-atom spacing and other ion pairs with a seven-atom spacing, the requirement of structural complementarity would not have been met. A full discussion of complementarity and structural compatibility may be found in U.S. Pat. Nos. 5,670,483 and 6,548,630. The definitions used therein and examples provided apply equally with respect to the present invention.

It should also be recognized that membranes may be formed from either a homogeneous mixture of peptides or a heterogeneous mixture of peptides. The term "homogeneous" in this context means peptides that are identical with one another. "Heterogeneous" indicates peptides that bind to one another but which are structurally different. Regardless of whether homogenous or heterogeneous peptides are used, the requirements with respect to the arrangement of amino acids, length, complementarity, and structural compatibility apply. In addition, it should be recognized that the carboxyl and amino groups of the terminal residues of peptides can either be protected or not protected using standard groups.

Making of Peptides

The self-assembling peptides of the present invention can be made by solid-phase peptide synthesis using standard N-tert-butyoxycarbonyl (t-Boc) chemistry and cycles using n-methylpyrolidone chemistry. Once peptides have been synthesized, they can be purified using procedures such as high pressure liquid chromatography on reverse-phase columns. Purity may also be assessed by HPLC and the presence of a correct composition can be determined by amino acid analysis.

Formation of Membranes

The self-assembling peptides described herein will not form membranes in water, but will assemble in the presence of a low concentration of monovalent metal cation. The order of effectiveness of these cations is $Li^+>Na^+>K^+>Cs^+$(U.S. Pat. No. 6,548,630). A concentration of monovalent cation of 5 mM should be sufficient for peptides to assemble and concentrations as high as 5 M should still be effective. The anion associated with the monovalent cation is not critical to the invention and can be acetate, chloride, sulfate, phosphate, etc. The PDGF-B will bind to the peptides at low salt concentration and will remain bound at concentrations sufficient to induce self assembly. Peptides can also form from self assembling peptides, and PDGF can attach, under conditions found in vivo. Therefore, it is possible to not only implant membranes, but also to implant either self-assembling peptides with attached PDGF or to co-implant self-assembling peptides and PDGF and to allow the membranes to form afterward. The term "implant" as used herein includes any method for introducing a membrane or peptides at a treatment site, including injection.

The initial concentration of peptide will influence the final size and thickness of membranes formed. In general, the higher the peptide concentration, the higher the extent of membrane formation. Formation can take place in peptide concentrations as low as 0.5 mM or 1 mg/ml. However, membranes are preferably formed at higher initial peptide concentrations, e.g., 10 mg/ml, to promote better handling characteristics. Overall, it is generally better to form membranes by adding peptides to a salt solution rather than adding salt to a peptide solution.

The formation of membranes is relatively unaffected by pH or by temperature. Nevertheless, pH should be maintained below 12 and temperatures should generally be in the range of 4-90° C. Divalent metal cations at concentrations equal to or above 100 mM result in improper membrane formation and should be avoided. Similarly, a concentration of sodium dodecyl sulfate of 0.1 % or higher should be avoided.

Membrane formation may be observed by simple visual inspection and this can be aided, if desired, with stains such as Congo Red. The integrity of membranes can also be observed microscopically, with or without stain.

PDGF

Platelet-derived growth factor (PDGF) normally exists as a dimer composed of two homologous but distinct peptides termed PDGF-A and -B chains, and may exist as AA, AB, and BB isoforms. Unless otherwise indicated the term "PDGF" and "PDGF-B" as used herein refer to any form of human PDGF in which the B chain is present, i.e., the term encompasses B monomers as well as AB and BB dimers. It also is expected that minor changes can be introduced into the structure of the B chain without disrupting its function or ability to bind to membranes and it may be possible to form fusion proteins or derivitized forms of the B chain that are still able to bind to membranes and have a positive therapeutic effect.

The full length amino acid sequence of PDGF has been known in the art for many years (see, Rao, et al., *Proc. Nat'l Acad. Sci. USA* 83:2392-2396 (1986)) and may be found, inter alia, as accession number P01127. The protein used herein can either be purchased commercially or synthesized using techniques well known in the art.

Pharmaceutical Compositions and Dosages

The compositions containing PDGF described above may be incorporated into a pharmaceutical composition containing a carrier such as saline, water, Ringer's solution and other agents or excipients. The dosage form will generally be designed for implantation or injection but topical dosage forms may be used in cases where the preparation will be used in the treatment of a wound or abrasion. All dosage forms may be prepared using methods that are standard in the art (see e.g., *Remington's Pharmaceutical Sciences,* 16th ed. A. Oslo. ed., Easton, Pa. (1980)).

It is expected that the skilled practitioner will adjust dosages on a case by case basis using methods well established in clinical medicine. General guidance concerning appropriate amounts of gel-immobilized PDGF to administer to heart patients is provided above. However, the amounts recited are simply guidelines since the actual dose will be carefully selected and adjusted by the attending physician based upon clinical factors unique to each patient. The optimal dosage will be determined by methods known in the art and will be influenced by factors such as the age of the patient, disease state and other clinically relevant factors.

EXAMPLES

I. Introduction

The present example demonstrates that protection of cardiomyocytes by endothelial cells is through PDGF-BB signaling. PDGF-BB induced cardiomyocyte Akt phosphorylation in a time- and dose-dependant manner and prevented apoptosis via $PI_3K$/Akt signaling. Using injectable self-assembling peptide nanofibers, which bound PDGF-BB in vitro, sustained delivery of PDGF-BB to the myocardium at the injected sites for 14 days was achieved. A blinded and randomized study of 96 rats showed that injecting nanofibers with PDGF-BB, but not nanofibers or PDGF-BB alone, decreased cardiomyocyte death and preserved systolic function after myocardial infarction. A separate blinded and randomized study in 52 rats showed that PDGF-BB delivered with nanofibers decreased infarct size after ischemia-reperfusion. PDGF-BB with nanofibers induced PDGFR-β and Akt phosphorylation in cardiomyocytes in vivo. These data demonstrate that endothelial cells protect cardiomyocytes via PDGF-BB signaling, and that this in vitro finding can be translated into an effective in vivo method of protecting myocardium after infarction. Furthermore, this study shows that injectable nanofibers allow precise and sustained delivery of proteins to the myocardium with potential therapeutic benefits.

II. Materials and Methods

Myocardial Cell Culture

Rat neonatal cardiomyocytes (1-2 days old) and adult cardiac endothelial cells and fibroblasts were isolated from Sprague-Dawley rats (Charles River Laboratories and Harlan) as previously described (Narmoneva, et al., *Circulation* 110:962 (2004)).

Cardiomyocyte Apoptosis Assays

Cardiomyocytes were plated at a density of $1.4×10^5$ cells/$cm^2$ overnight, cultured in serum-free DMEM for 24 hours, and then subjected to 10 mM chelerythrine, 1 mM doxorubicin (both from Sigma-Aldrich), or 0.2 mM $H_2O_2$ plus 100 ng/ml TNF-α (PeproTech) for another 24 hours with or without treatment with human PDGF-BB (PeproTech). In coculture experiments, before plating of cardiomyocytes, cardiac endothelial cells or fibroblasts were cultured until subconfluent. TUNEL staining was performed using a TUNEL staining kit (Roche Diagnostics Corp.). For DNA fragmentation experiments, cells were trypsinized, fixed with 80% ethanol at −20° C. for 2 hours, incubated in 0.1 mg/ml RNase (Sigma-Aldrich) at 37° C. for 30 minutes, stained with 0.1 mg/ml propidium iodide (Sigma-Aldrich) for 10 minutes, and then subjected to flow cytometry (Cytomics FC 500; Beckman Coulter). The Annexin-V cell sorting method was performed using an apoptosis assay kit (Vybrant Apoptosis Assay Kit #3; Molecular Probes, Invitrogen Corp.) following the manufacturer's instructions. The dosages for neutralizing antibodies were 0.4 μg/ml anti-PDGF-BB, 2 μg/ml anti-PDGFR-β, 2 μg/ml anti-PDGF-AA, and 20 μg/ml anti-PDGFR-a (all from Sigma-Aldrich except anti-PDGF-AA from R&D Systems), and the dosage of PDGF-BB was 10 ng/ml unless otherwise indicated. Adenoviral transfection was performed as previously described by Fujio and Walsh (Fujio, et al., *J Biol. Chem.* 274:16349-16354 (1999)). Each experiment was performed in triplicate and repeated at least 3 times using different primary cell preparations.

Western Blot Analysis

Whole-cell extracts were collected using lysis buffer containing 1% (wt/vol) SDS, 50 mM Tris-Cl (pH 7.4), 5 mM EDTA supplemented with 4× sample buffer (Invitrogen Corp.) and proteinase inhibitor cocktail (Sigma-Aldrich) at 1:500 dilution. The following antibodies were used: anti-PDGFR-β (Santa Cruz Biotechnology Inc.), anti-phospho-PDGFR-β, anti-Akt, anti-phospho-Akt, anti-phospho-ERK, anti-phosphop38, and anti-jun N-terminal kinase (all from Cell Signaling Technology).

Immunocytochemistry

For immunocytochemical staining of PDGFR-μ activation, cardiomyocytes were prepared using the same method as described above using anti-phospho-PDGFR-μ antibody (Cell Signaling Technology).

Protein Binding Assay of Self-assembling NFs

NFs were prepared as previously described (Narmoneva, et al., *Circulation* 110:962 (2004), and PBS or 100 ng of BSA (Sigma-Aldrich), PDGF-BB (PeproTech), VEGF-A, bFGF, or angiopoietin-1 (all from R&D Systems) was embedded in NFs. NFs were incubated with PBS (100 μl) at 37° C. for 3 hours. Supernatant (PBS after incubation) was collected and subjected to Bradford protein assay. In parallel experiments, the same amount of proteins was added in PBS but not embedded within NFs, in order to demonstrate that the experimental binding conditions were at equilibrium.

MI and Injection of Peptide NFs

All animal protocols were approved by the Harvard Medical School Standing Committee on Animals. MI was produced in approximately 250-g male Sprague-Dawley rats (Charles River Laboratories and Harlan). Briefly, rats were anesthetized by pentobarbital and, following tracheal intubation, the hearts were exposed via left thoracotomy. The left coronary artery was identified after pericardiotomy and was ligated by suturing with 6-0 prolene at the location approximately 3 mm below the left atrial appendix. For the sham operation, suturing was performed without ligation. Peptide NFs (peptide sequence AcN-RARADADARARADADA-CNH2 (SEQ ID NO:35); from SynPep Corp.) with or without 50 or 100 ng/ml human PDGF-BB (PeproTech) and/or 50 mM LY294002 (Calbiochem) were dissolved in 295 mM sucrose and sonicated to produce a 1% solution for injection.

A total of 80 μl of self-assembling peptide NFs was injected into the infarcted border zone through 3 directions (equal amount for each injection) immediately after coronary artery ligation (FIG. 1). Injections were completed within 1 minute after coronary ligation. Following injection, the chest was closed, and animals were allowed to recover under a heating pad. For the PDGF-BB retention study (120 surviving rats), animals were sacrificed after 10 minutes, 1 day, 3 days, or 14 days.

For the functional and histological studies (126 surviving rats), rats were euthanized after 1, 14, or 28 days. For the PI3K/Akt blocking (16 surviving rats) and infarct size (64 surviving rats) studies, hearts were harvested after 24 hours. For the myocardial regional blood flow study (30 surviving rats), hearts were harvested for microsphere collection after 14 days. All of the procedures were performed in a blinded and randomized manner, and data were analyzed after there were at least 6 animals in each coded group. The overall surgical mortality rate in this study was 5.3% (20 of 376 rats, with 356 surviving rats for the study cohorts).

ELISA

For the in vivo PDGF-BB delivery study, myocardial protein was extracted from injected sites using a nonreducing buffer containing 1% Triton X-100, 50 mM Tris (pH 7.4), 300 mM NaCl, 5 mM EDTA, and 0.02% NaN3 supplemented with proteinase inhibitor cocktail (Sigma-Aldrich) at 1:200 dilution. The same amount of protein from each heart was loaded in triplicate for anti-human PDGF-BB ELISA following the manufacturer's instructions (R&D Systems).

Fluorescence Microscopy

Fixed myocardial sections were deparaffinized, rehydrated, and pretreated with boiling 10 mM sodium citrate (pH 7.2) for 10 minutes and 10 mg/ml proteinase K (Sigma-Aldrich) at room temperature for 10 minutes, followed by incubation with antibodies against phospho-PDGFR-β, cleaved caspase-3 (both from Cell Signaling Technology), Ki67 (Abcam), isolectin (Molecular Probes; Invitrogen Corp.), α-SMA, tropomyosin, vimentin (all from Sigma-Aldrich) at 4° C. overnight, and then Alexa Fluor-conjugated secondary antibodies (Molecular Probes; Invitrogen Corp.). Sections were next incubated with anti-α-sarcomeric actinin or tropomyosin (Sigma-Aldrich), followed with different Alexa Fluor secondary antibodies to obtain different fluorescence colors. After counterstaining with DAPI, sections were mounted and observed under fluorescence microscopy. For the vascular diameter measurement, sections were stained with isolectin or α-SMA and photographed, and the diameter was measured using Image-Pro version 4.5 (MediaCybernetics).

Echocardiography

Echocardiographic acquisition and analysis were performed as previously described Lindsey, et al., *Circulation* 105:753-758 (2002)). Left ventricular fractional shortening was calculated as (EDD-ESD)/EDD×100%, where EDD is end-diastolic dimension and ESD is end-systolic dimension.

Immunohistochemistry

Formalin-fixed, paraffin-embedded sections were prepared for immunohisto-chemistry as previously described (Davis, et al., *Circulation* 111:442-450 (2005); Weinberg, et al., *Am. J. Physiol. Heart Circ. Physiol.* 288:H1 802-H1 809 (2005)). The first antibodies used were anti-phospho-PDGFR-β, anti-phospho-Akt, anti-cleaved caspase-3 (all from Cell Signaling Technology), anti-neutrophil (Serotec), anti-mac3 (BD Biosciences), and anti-BrdU (Roche Diagnostics Corp.).

Myocardial I/R and Measurement of Infarct Size

Myocardial I/R and measurement of infarct size, as described previously (Weinberg, et al., *Am. J. Physiol. Heart*

*Circ. Physiol.* 288:H1802-H1809 (2005)), were performed in rats. The ischemia time was 60 minutes and reperfusion period 24 hours. All of the procedures were performed in a blinded and randomized manner, and there were at least 6 animals in each group.

BrdU Protocol

Two hours before sacrifice, 50 mg/kg body weight of BrdU (Sigma-Aldrich) was injected i.p. in rats. BrdU staining was performed using the method described by Geary et al. (Geary, et al., *Circulation* 91:2972-2981 (1995)). A piece of small gut from each animal was used for positive control.

DNA Synthesis

Cell proliferation was measured using [$^3$H]thymidine incorporation into DNA as previously described (Schulze, et al., *Circ. Res.* 91:689-695 (2002)).

Myocardial Regional Blood Flow Measurement

Myocardial regional blood flow was measured using fluorescent microspheres as described by Van Oosterhout et al. (Van Oosterhout, et al., *Am. J. Physiol.* 269:H725-H733 (1995)) with modifications. Briefly, animals received heparin (about 2 U/g body weight) and were anesthetized. The entire heart was exposed via left thoracotomy, and the descending aorta was opened to insert a withdrawal catheter connecting to a bidirectional rolling pump. Blood was withdrawn at a rate of 1-2 ml/min for 2 minutes, starting 5 seconds before injection of fluorescent microspheres into the left atrium. The blood was transferred to a collecting tube containing 2 mg of EDTA, and the total amount was recorded. A total 30 μl of microspheres, a mixture of equal amount of blue-green (10-μm diameter; $3.6\times10^4$ beads), green (15-μm diameter; $1\times10^4$ beads), and yellow-green (10-μm diameter; $3.6\times10^4$) beads (all from Molecular Probes; Invitrogen Corp.), was injected for each rat. Animals were sacrificed 2 minutes after injection. After removing the entire heart, the infarcted myocardium at the left ventricle was identified, harvested, weighed, and stored at 4° C. A similar size of myocardium from the noninfarcted right ventricle was also harvested as a control. The blood and myocardium were then digested in 4 N KOH (>3×volume of samples) at 50° C. for overnight. After centrifuging at 2,000 g for 10 minutes, the pellet that contained microspheres was washed twice with 0.25% Tween-20 and then distilled water. The pellet was dissolved with 0.5 ml xylene and then incubated at 50° C. for 3 hours with intermittent vortex and sonication. The supernatant was collected and subjected to measurement of fluorescence intensity (Victor$^2$; PerkinElmer) with triplicates for each sample. The myocardial regional blood flow was calculated using the formula $Q_i=(Q_{ref} \times F_i) \div F_{ref}$, where $Q_i$ and $Q_{ref}$ are the flow rates in samples and the reference withdrawal speed, respectively, and $F_i$ and $F_{ref}$ are the fluorescence intensity in myocardial samples and in the reference blood samples. After normalizing with weight, the absolute myocardial blood flow was expressed in milliliters/minute/gram.

Statistics

All data are expressed as mean ±SEM. Statistical significance was determined using the 2-tailed Student's t test or ANOVA as appropriate. Differences between groups were considered statistically significant at P<0.05.

III. Results

Endothelial Cells Promote Cardiomyocyte Survival via PDGF-BB/PDGFR-β Signaling

Previous studies demonstrated that endothelial cells can prevent cardiomyocyte apoptosis in coculture (Narmoneva, et al., *Circulation* 110:962-968 (2004); Kuramochi, et al., *J. Biol. Chem.* 279:51141-51147 (2004)), a finding we explored further to establish conditions for quantitative delivery in vivo. Neonatal rat cardiomyocytes were cocultured with adult cardiac endothelial cells or fibroblasts, and cardiomyocyte apoptosis was induced by 3 different methods, including treatment with doxorubicin, chelerythrine, and $H_2O_2$ plus TNF-α. Apoptosis was quantified with 3 independent assays, including in situ TUNEL staining, DNA fragmentation by propidium iodide staining, and annexin-V cell sorting. With each apoptotic stimulus, coculture with endothelial cells, but not fibroblasts, prevented cardiomyocyte apoptosis. The protection of cardiomyocytes from apoptosis in cardiomyocyte-endothelial coculture was blocked by neutralizing antibodies against PDGF-BB or PDGFR-β, but not by antibodies against PDGF-AA or PDGFR-α, indicating that endothelium-derived cardiomyocyte protection occurs through the PDGF-BB/PDGFR-β pathway.

PDGF-BB Prevents Cardiomyocyte Apoptosis via PI3K/Akt Signaling

To evaluate further the effects of PDGF-BB in cardiomyocyte apoptosis, we induced cardiomyocyte apoptosis by multiple methods with or without PDGF-BB and quantified apoptosis with 3 independent assays as described above. PDGF-BB prevented cardiomyocyte apoptosis irrespective of stimulus or assay, and there was a dose dependent antiapoptotic effect, with optimal results at PDGF-BB concentrations of 10 ng/ml and higher. PDGF-BB, but not PDGF-AA, induced phosphorylation of PDGFR-β, and the downstream kinase Akt in cardiomyocytes in a dose- and time-dependent manner but induced no significant activation of p42/p44 (ERK-½), p38, or jun N-terminal kinase from 5 to 60 minutes. Immunofluorescence costaining of phospho-PDGFR-β and α-sarcomeric actinin confirmed the activation and internalization of PDGFR-β in differentiated cardiomyocytes by PDGF-BB. Blocking Akt signaling using a PI3K-specific inhibitor (LY294002) or a dominant-negative Akt adenovirus abolished the prosurvival effect of PDGF-BB in cardiomyocytes, demonstrating that cardiomyocyte protection of PDGF-BB may occur via the PI3K/Akt pathway. These results show that PDGF-BB is a potential candidate cardiomyocyte survival factor for targeted delivery into the myocardium.

Controlled Intramyocardial Delivery of PDGF-BB Using Injectable Self-assembling Peptide NFs To explore the possibility of using self assembling peptide NFs for controlled intramyocardial delivery of PDGF-BB, we first tested the binding capability of PDGF-BB by peptide NFs. Although these NFs do not have specific binding motifs for peptides, they are amphiphilic, with the potential to bind other proteins through weak molecular interactions. When PDGF-BB (100 ng total) was embedded with the NFs, the binding capacity was 1 ng PDGF-BB per microgram of NFs. This binding capacity was 10-fold higher than the amount of PDGF-BB per mass of NFs used in subsequent experiments in vivo (described below). We observed similar binding of other growth factors, including VEGF-A, bFGF, and angiopoietin-1, all of which bound significantly better to the peptide NFs than BSA.

To assess the feasibility of delivering PDGF-BB with self-assembling peptide NFs into the myocardium for cardioprotection, we injected PDGF-BB with peptide NFs into the myocardium of rats. All of the procedures were blinded and randomized, with at least 6 animals in each group. Left coronary arteries were ligated, immediately followed by direct myocardial injection of 1% peptide NFs (peptide sequence AcN-RARADADARARADADA-CNH2 (SEQ ID NO:35) with or without PDGF-BB into the infarcted border zones at 3 locations. Protein extracted from the injected region was assayed by ELISA specific for human PDGF-BB. Human PDGF-BB was undetectable in rats with sham operation only, MI only, or MI with NFs (MI+NFs) only.

Ten minutes after injecting 4 ng human PDGF-BB with or without peptide NFs, most of PDGF-BB was retained in the injected region in both groups (79.5%±18.3% in the group without peptide NFs and 91.8%±6.4% in the group with peptide NFs; P>0.05). Without peptide NFs, PDGF-BB rapidly disappeared from the injected sites after 24 hours, and only a negligible amount of PDGF-BB could be detected after 3 days. In contrast, with peptide NFs, PDGF-BB was retained at the injected sites; 16.1%±2.4% of PDGF-BB remained at the targeted delivery sites after 14 days (P<0.001 for PDGF-BB with NFs versus PDGF-BB without NFs at 1-, 3-, and 14-day time points).

Immunohistochemical staining showed phosphorylation of PDGFR-$\beta$ at the injected sites by NF/PDGF-BB, but not by NFs or PDGF-BB alone or in the sham or MI only after 14 days. Immunofluorescence costaining confirmed sustained activation of PDGFR-$\beta$ in cardiomyocytes adjacent to the injected areas after 14 days. Furthermore, to determine more quantitatively the difference in PDGFR-$\beta$ and Akt phosphorylation between groups, we used Western blotting to examine protein extracted from the injected sites and found sustained PDGFR-$\beta$ and Akt phosphorylation 1 and 14 days after injection of NFs with PDGF-BB (NF/PDGF-BB). Injection of PDGF-BB alone slightly induced PDGFR-$\beta$ and Akt phosphorylation after 1 day, but both disappeared by day 14.

These results demonstrate that injectable self-assembling peptide NFs can successfully deliver PDGF-BB into the myocardium, leading to prolonged activation of the PDGF signaling pathway in cardiomyocytes in vivo.

Injection of NF/PDGF-BB Preserves Myocardial Function

To examine the functional effects of injecting self-assembling peptide NF/PDGF-BB for cardioprotection, we then performed a blinded and randomized study in 96 rats, with at least 6 animals in each experimental group. Two doses of PDGF-BB (50 and 100 ng/ml [P50 and P100]) were selected for injection, estimated to deliver approximate PDGF-BB concentrations in the infarcted myocardium of 10 and 20 ng/ml, respectively, by injecting a total of 80 µl (given at 3 different injection sites) of NF/PDGF-BB into 400 mg of infarcted myocardium.

Twenty-four hours after MI, left ventricular fractional shortening decreased as anticipated compared with sham-operated myocardium (43.1%±7.7% in the sham group versus 27.5%±5.6% in the MI group; P<0.05), and injection of NFs or PDGF-BB alone did not significantly improve fractional shortening. However, in infarcted hearts with injection of NF/P50 or NF/P100, fractional shortening significantly improved (42.7%±7.1% and 43.0%±8.4%, respectively; P<0.05 for both versus MI or MI+NFs).

At day 14 after infarction, improvement of fractional shortening was maintained in hearts that received NF/P100, but not in hearts that received NF/P50 (50.0%±8.7% in sham, 32.8%±4.2% after MI, 39.6%±7.9% in NF/P50, and 47.6%±10.0% in NF/P100; P<0.05 for sham versus MI and NF/P100 versus MI or MI+NFs), implying dose-dependent cardioprotection by sustained release of PDGF-BB from the peptide NFs. Consistent with the improvement of fractional shortening after infarction, injection of NF/PDGF-BB also prevented cardiac dilation as measured by ventricular end-systolic and end-diastolic dimensions (P<0.05).

Using trichrome staining, we did not observe an increase in fibrosis by injection of NF/PDGF-BB, suggesting that injection of NF/PDGF-BB may not stimulate cardiac fibroblasts (Ponten, et al., *Am. J. Pathol.* 163:673-682 (2003)).

Injection of NF/PDGF-BB Decreases Cardiomyocyte Apoptosis and Induces PI3K/Akt Activation After Infarction To address whether preservation of cardiac systolic function by injection of peptide NF/PDGF-BB was accompanied by prevention of cardiomyocyte apoptosis, we examined tissues using immunofluorescence costaining of cleaved caspase-3 and $\alpha$-sarcomeric actinin. Injection of peptide NFs with 50 or 100 ng/ml PDGF-BB, but not NFs or PDGF-BB alone, dramatically decreased caspase-3 activation after 1 day (P<0.001 for 50 or 100 ng/ml PDGF-BB with NFs versus MI or MI+NFs). After 14 days, injection of NF/P100 reduced apoptosis more than injection of NF/P50, although both treatments significantly reduced apoptosis compared with controls (0.5%±0.2% in sham, 12.8%±1.1% in MI, 7.2%±0.8% in NFs with 50 ng/ml of PDGF-BB, P<0.01 versus MI; and 3.1%±0.4% in NFs with 100 ng/ml of PDGF-BB, P<0.001 versus MI). Furthermore, we demonstrated activation of Akt in the myocardium by injection of NF/PDGF-BB but not when NFs or PDGF-BB alone was injected, showing that this strategy induces survival signaling in the myocardium in vivo (Matsui, et al., *Circulation* 104:330-335(2001); Mangi, et al., *Nat. Med.* 9:1195-1201 (2003); Bock-Marquette, et al., *Nature* 432:466-472 (2004)).

With addition of the PI3K-specific inhibitor LY294002 (50 µM) in peptide NF/PDGFBB, we found that Akt activation was blocked and improvement of fractional shortening by injection of NF/PDGF-BB was also abolished, implying that PI3K/Akt signaling may play a role in the cardioprotective effect of injecting peptide NF/PDGF-BB. Moreover, as multiple myocardial cells may be targets for PDGF-BB, we examined Akt phosphorylation in cardiomyocytes, endothelial cells, VSMCs, and fibroblasts after injection of NF/PDGF-BB using immunofluorescence costaining of phospho-Akt and cell-specific markers. We found that Akt phosphorylation was induced in cardiomyocytes after 1 and 14 days and also in endothelial cells after 14 days of injection. However, we were not able to detect Akt phosphorylation in VSMCs or fibroblasts. These results imply that cardiomyocytes are the main targets for PDGF-BB after injection of NF/PDGF-BB.

Injection of NF/PDGF-BB Decreases Infarct Size After I/R Injury

To investigate whether injection of NF/PDGF-BB may also benefit the heart from ischemia/reperfusion (I/R) injury, we conducted another blinded and randomized experiment in 52 rats to examine infarct size after 60-minute ischemia and 24-hour reperfusion (n=10 in sham and I/R alone groups; n=16 in I/R+NFs alone and I/R+NF/PDGF-BB groups). Injection of NF/P100, but not NFs alone, improved ventricular fractional shortening after 24 hours of reperfusion (50.3%±2.0% in sham, 36.1%±2.0% in I/R only, 41.9%±2.4% in I/R+NFs, and 51.3%±2.1% in I/R+NF/PDGF-BB; P<0.05 for I/R+NF/PDGF-BB versus I/R only or I/R+NFs). Infarct size, represented by percent of area at risk, was also decreased by injection of NF/PDGF-BB (0% in sham, 40.0%±2.3% in I/R only, 38.5%±2.2% in I/R+NFs, and 27.8%±2.4% in I/R+NF/PDGF-BB; P<0.01 for I/R+NF/PDGFBB versus I/R only or I/R+NFs).

As expected, the area at risk, represented by the percentage volume of the left ventricle, was similar in I/R only, I/R+NFs, and I/R+NF/PDGF-BB groups, indicating that the location of coronary ligation was similar among the groups. We also generated a new randomized and blinded experiment to study the effects of PDGF-BB alone on infarct size (6 rats for I/R only and 6 rats for I/R+PDGF-BB) and did not observe statistical difference between these 2 groups (P=0.645). Taken together, these results demonstrate that injection of NF/PDGF-BB may preserve myocardial function after infarction and I/R injuries.

Injection of NF/PDGF-BB Does Not Increase Myocardial Cell Proliferation Neovascularization, Regional Blood Flow, or Inflammation After Infarction Since PDGF-BB is a potent mitogen for many cells, we studied cell proliferation induced by PDGF-BB delivery in the infarcted myocardium using BrdU and Ki67 to label proliferative cells. Active cell proliferation could be detected in the positive control, rat small intestine, by BrdU staining. In contrast, less than 0.5% cells were BrdU positive in the periinfarct myocardium after 1, 14, and 28 days, and there were no differences in number of BrdU-positive cells among all of the study groups. Similar results were found using Ki67 staining.

Interestingly, costaining Ki67 and cell-specific markers revealed that cell proliferation occurred only in endothelial cells and fibroblasts, but not in cardiomyocytes or VSMCs, and there were no differences in numbers of Ki67-positive cells between groups. Consistent with these results, using [$^3$H]thymidine incorporation assay, we found PDGF-BB did not induce DNA synthesis in cultured rat cardiomyocytes or cardiac fibroblasts but did increase DNA synthesis in human aortic smooth muscle cells. These results suggest that injection of NF/PDGF-BB does not induce cell proliferation in the ischemic myocardium.

We then tested whether injection of NF/PDGF-BB could enhance neovascularization in the ischemic myocardium because we have previously found that injection of NFs alone in normal myocardium led to neovascularization within the NFs (Davis, et al., *Circulation* 111:442-450 (2005)). The overall capillary (endothelial cell staining) and arterial (VSMC staining) densities (vessel number per millimeter$^2$) in the periinfarct area were not changed by injection of NFs, with or without PDGF-BB, after 14 and 28 days of infarction. Vascular diameters were also not different between groups. Consistent with these data, using fluorescent microspheres, we found that regional blood flow in the myocardium was decreased 14 days after infarction, but not changed by injection of NF/PDGF-BB, NFs alone, or PDGF-BB alone.

We also examined whether injection of NFs with or without PDGF-BB could trigger an inflammatory response and found that there was no increase in neutrophil or monocyte/macrophage infiltration after injection compared with MI without injection of NFs.

Together these data suggest that improvement of cardiac function by NF/PDGF-BB injection may not result from improvement of blood supply.

III. Discussion

Given the rapid loss of cardiomyocytes after ischemic injury, promoting cardiomyocyte survival is an efficient strategy for preserving viable myocardium. The principal findings of this study are that PDGF-BB is an endothelium-secreted paracrine factor with direct antiapoptotic effects in cardiomyocytes and that this prosurvival signal can be delivered into the infarcted myocardium for cardioprotection in a highly controlled manner using injectable self-assembling peptide NFs.

The results show that this strategy is highly effective for delivery of PDGF-BB in the early period after infarction; even after 14 days, 16% of PDGF-BB still remained in the injected sites. Compared with injection of PDGF-BB alone, which was rapidly eliminated after injection, NF/PDGF-BB injection achieved sustained delivery of PDGF-BB inside the myocardium. Importantly, PDGF-BB embedded within the NFs remained biologically active after 14 days of injection, inducing phosphorylation of PDGFR-$\beta$ and Akt in cardiomyocytes through the entire layer of myocardium at the injected areas and, occasionally, even into the papillary muscles.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of treating a patient who has had a myocardial infarction; wound; damaged ligament, tendon or cartilage; or damaged nerve tissue, comprising: administering to said patient a pharmaceutical composition comprising a biologically compatible peptide membrane, wherein
   a) said biologically compatible peptide membrane comprises self-assembling peptides, wherein said self-assembling peptides:
      i) are 12-200 amino acids in length;
      ii) have alternating hydrophobic and hydrophilic amino acids;
      iii) are complementary; and
      iv) are structurally compatible;
   (b) at least 0.1% of said self-assembling peptides are bound directly to PDGF; and
   (c) said pharmaceutical composition is devoid of cells.

2. The method of claim 1 wherein said method is a treatment for myocardial infarction.

3. The method of claim 1 wherein said method is a treatment for a wound.

4. The method of claim 1 wherein said method is a treatment for a damaged ligament, tendon or cartilage.

5. The method of claim 1 wherein said method is a treatment for damaged nerve tissue.

6. The method of claim 1, wherein said biologically compatible peptide membrane consists of self-assembling peptides, wherein:

a) said peptides are 12-24 amino acids in length; and
   b) 0.5-10% of said peptides are bound to PDGF.

7. The method of claim 1, wherein said self-assembling peptides are homogeneous.

8. The method of claim 1, wherein said self-assembling peptides are selected from the group consisting of:

| Sequence | SEQ ID |
|---|---|
| AKAKAEAEAKAKAEAE, | (SEQ ID NO:1); |
| AKAEAKAEAKAEAKAE, | (SEQ ID NO:2); |
| EAKAEAKAEAKAEAKA, | (SEQ ID NO:3); |
| KAEAKAEAKAEAKAEA, | (SEQ ID NO:4); |
| AEAKAEAKAEAKAEAK, | (SEQ ID NO:5); |
| ADADARARADADARAR, | (SEQ ID NO:6); |
| ARADARADARADARAD, | (SEQ ID NO:7); |
| DARADARADARADARA, | (SEQ ID NO:8); |
| RADARADARADARADA, | (SEQ ID NO:9); |
| ADARADARADARADAR, | (SEQ ID NO:10); |
| ARADAKAEARADAKAE, | (SEQ ID NO:11); |
| AKAEARADAKAEARAD, | (SEQ ID NO:12); |
| ARAKADAEARAKADAE, | (SEQ ID NO:13); |

-continued

| | |
|---|---|
| AKARAEADAKARADAE, | (SEQ ID NO:14); |
| AQAQAQAQAQAQAQ, | (SEQ ID NO:15); |
| VQVQVQVQVQVQVQ, | (SEQ ID NO:16); |
| YQYQYQYQYQYQYQ, | (SEQ ID NO:17); |
| HQHQHQHQHQHQHQ, | (SEQ ID NO:18); |
| ANANANANANANAN, | (SEQ ID NO:19); |
| VNVNVNVNVNVNVN, | (SEQ ID NO:20); |
| YNYNYNYNYNYNYN, | (SEQ ID NO:21); |
| HNHNHNHNHNHNHN, | (SEQ ID NO:22); |
| ANAQANAQANAQANAQ, | (SEQ ID NO:23); |
| AQANAQANAQANAQAN, | (SEQ ID NO:24); |
| VNVQVNVQVNVQVNVQ, | (SEQ ID NO:25); |
| VQVNVQVNVQVNVQVN, | (SEQ ID NO:26); |
| YNYQYNYQYNYQYNYQ, | (SEQ ID NO:27); |
| YQYNYQYNYQYNYQYN, | (SEQ ID NO:28); |
| HNHQHNHQHNHQHNHQ, | (SEQ ID NO:29); |
| HQHNHQHNHQHNHQHN, | (SEQ ID NO:30); |
| AKAQADAKAQADAKAQAD, | (SEQ ID NO:31); |
| VKVQVDVKVQVDVKVQVD, | (SEQ ID NO:32); |
| YKYQYDYKYQYDYKYQYD, | (SEQ ID NO:33); |
| HKHQHDHKHQHDHKHQHD, | (SEQ ID NO:34); |
| RARADADARARADADA, | (SEQ ID NO:35); |
| RADARGDARADARGDA, | (SEQ ID NO:36); |
| RAEARAEARAEARAEA, | (SEQ ID NO:37); |
| KADAKADAKADAKADA, | (SEQ ID NO:38); |
| AEAEAHAHAEAEAHAH, | (SEQ ID NO:39); |
| FEFEFKFKFEFEFKFK, | (SEQ ID NO:40); |
| LELELKLKLELELKLK, | (SEQ ID NO:41); |
| AEAEAKAKAEAEAKAK, | (SEQ ID NO:42); |
| AEAEAEAEAKAK, | (SEQ ID NO:43); |
| KAKAKAKAEAEAEA, | (SEQ ID NO:44); |
| AEAEAEAEAKAKAKAK, | (SEQ ID NO:45); |
| RARARARADADADADA, | (SEQ ID NO:46); |
| ADADADADARARARAR, | (SEQ ID NO:47); |
| DADADADARARARARA, | (SEQ ID NO:48); |
| HEHEHKHKHEHEHKHK, | (SEQ ID NO:49); |
| VEVEVEVEVEVEVEVE, and | (SEQ ID NO:50); |
| RFRFRFRFRFRFRFRF, | (SEQ ID NO:51). |

9. The method of claim 8, wherein said method is a treatment for myocardial infarction.

10. The method of claim 8, wherein said method is a treatment for a wound.

11. The method of claim 8, wherein said method is a treatment for a damaged ligament, tendon or cartilage.

12. The method of claim 8, wherein said method is a treatment for damaged nerve tissue.

13. The method of claim 1, wherein said self-assembling peptides are homogeneous and have a structure selected from the group consisting of: (RARADADA)$_n$ (SEQ ID NO:53); (ARARADAD) (SEQ ID NO:89); and (RADARADA)$_n$ (SEQ ID NO:54); wherein n=2-10.

14. The method of claim 13, wherein said method is a treatment for myocardial infarction.

15. The method of claim 13, wherein said method is a treatment for a wound.

16. The method of claim 13, wherein said method is a treatment for a damaged ligament, tendon or cartilage.

17. The method of claim 13, wherein said method is a treatment for damaged nerve tissue.

18. The method of claim 1, wherein said self-assembling peptides are homogeneous and have the structure (AEAEAKAK)$_n$ (SEQ ID NO:55), wherein n=2-10.

19. The method of claim 1, wherein said biologically compatible peptide membrane, is made by a process comprising: combining human PDFG with one or more peptides in an aqueous medium at a concentration of monovalent metal cation that is sufficient to promote the self-assembly of said peptides and wherein said one or more peptides are selected from the group consisting of:

| | |
|---|---|
| AKAKAEAEAKAKAEAE, | (SEQ ID NO:1); |
| AKAEAKAEAKAEAKAE, | (SEQ ID NO:2); |
| EAKAEAKAEAKAEAKA, | (SEQ ID NO:3); |
| KAEAKAEAKAEAKAEA, | (SEQ ID NO:4); |
| AEAKAEAKAEAKAEAK, | (SEQ ID NO:5); |
| ADADARARADADARAR, | (SEQ ID NO:6); |
| ARADARADARADARAD, | (SEQ ID NO:7); |
| DARADARADARADARA, | (SEQ ID NO:8); |
| RADARADARADARADA, | (SEQ ID NO:9); |
| ADARADARADARADAR, | (SEQ ID NO:10); |
| ARADAKAEARADAKAE, | (SEQ ID NO:11); |
| AKAEARADAKAEARAD, | (SEQ ID NO:12); |
| ARAKADAEARAKADAE, | (SEQ ID NO:13); |
| AKARAEADAKARADAE, | (SEQ ID NO:14); |
| AQAQAQAQAQAQAQ, | (SEQ ID NO:15); |
| VQVQVQVQVQVQVQ, | (SEQ ID NO:16); |
| YQYQYQYQYQYQYQ, | (SEQ ID NO:17); |
| HQHQHQHQHQHQHQ, | (SEQ ID NO:18); |
| ANANANANANANAN, | (SEQ ID NO:19); |
| VNVNVNVNVNVNVN, | (SEQ ID NO:20); |
| YNYNYNYNYNYNYN, | (SEQ ID NO:21); |
| HNHNHNHNHNHNHN, | (SEQ ID NO:22); |

| | |
|---|---|
| ANAQANAQANAQANAQ, | (SEQ ID NO:23); |
| AQANAQANAQANAQAN, | (SEQ ID NO:24); |
| VNVQVNVQVNVQVNVQ, | (SEQ ID NO:25); |
| VQVNVQVNVQVNVQVN, | (SEQ ID NO:26); |
| YNYQYNYQYNYQYNYQ, | (SEQ ID NO:27); |
| YQYNYQYNYQYNYQYN, | (SEQ ID NO:28); |
| HNHQHNHQHNHQHNHQ, | (SEQ ID NO:29); |
| HQHNHQHNHQHNHQHN, | (SEQ ID NO:30); |
| AKAQADAKAQADAKAQAD, | (SEQ ID NO:31); |
| VKVQVDVKVQVDVKVQVD, | (SEQ ID NO:32); |
| YKYQYDYKYQYDYKYQYD, | (SEQ ID NO:33); |
| HKLHQHDHKHQHDHKHQHD, | (SEQ ID NO:34); |
| RARADADARARADADA, | (SEQ ID NO:35); |
| RADARGDARADARGDA, | (SEQ ID NO:36); |
| RAEARAEARAEARAEA, | (SEQ ID NO:37); |
| KADAKADAKADAKADA, | (SEQ ID NO:38); |
| AEAEAHAHAEAEAHAH, | (SEQ ID NO:39); |
| FEFEFKFKFEFEFKFK, | (SEQ ID NO:40); |
| LELELKLKLELELKLK, | (SEQ ID NO:41); |
| AEAEAKAKAEAEAKAK, | (SEQ ID NO:42); |
| AEAEAEAEAKAK, | (SEQ ID NO:43); |
| KAKAKAKAEAEAEAEA, | (SEQ ID NO:44); |
| AEAEAEAEAKAKAKAK, | (SEQ ID NO:45); |
| RARARARADADADADA, | (SEQ ID NO:46); |
| ADADADADARARARAR, | (SEQ ID NO:47); |
| DADADADARARARARA, | (SEQ ID NO:48); |
| HEHEHKHKLHEHEHKHK, | (SEQ ID NO:49); |
| VEVEVEVEVEVEVEVEVE, and | (SEQ ID NO:50); |
| RFRFRFRFRFRFRFRFRF, | (SEQ ID NO:51). |

20. The method of claim 19, wherein said monovalent metal cation is selected from the group consisting of: lithium; sodium; and potassium.

* * * * *

SEQUENCE LISTING

```
<160> NUMBER OF SEQ ID NOS: 89

<210> SEQ ID NO 1
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 1

Ala Lys Ala Lys Ala Glu Ala Glu Ala Lys Ala Lys Ala Glu Ala Glu
1               5                   10                  15

<210> SEQ ID NO 2
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 2

Ala Lys Ala Glu Ala Lys Ala Glu Ala Lys Ala Glu Ala Lys Ala Glu
1               5                   10                  15
```

```
<210> SEQ ID NO 3
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 3

Glu Ala Lys Ala Glu Ala Lys Ala Glu Ala Lys Ala Glu Ala Lys Ala
 1               5                   10                  15

<210> SEQ ID NO 4
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 4

Lys Ala Glu Ala Lys Ala Glu Ala Lys Ala Glu Ala Lys Ala Glu Ala
 1               5                   10                  15

<210> SEQ ID NO 5
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 5

Ala Glu Ala Lys Ala Glu Ala Lys Ala Glu Ala Lys Ala Glu Ala Lys
 1               5                   10                  15

<210> SEQ ID NO 6
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 6

Ala Asp Ala Asp Ala Arg Ala Arg Ala Asp Ala Asp Ala Arg Ala Arg
 1               5                   10                  15

<210> SEQ ID NO 7
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 7

Ala Arg Ala Asp Ala Arg Ala Asp Ala Arg Ala Asp Ala Arg Ala Asp
 1               5                   10                  15

<210> SEQ ID NO 8
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 8

Asp Ala Arg Ala Asp Ala Arg Ala Asp Ala Arg Ala Asp Ala Arg Ala
 1               5                   10                  15
```

```
<210> SEQ ID NO 9
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 9

Arg Ala Asp Ala Arg Ala Asp Ala Arg Ala Asp Ala Arg Ala Asp Ala
1               5                   10                  15

<210> SEQ ID NO 10
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 10

Ala Asp Ala Arg Ala Asp Ala Arg Ala Asp Ala Arg Ala Asp Ala Arg
1               5                   10                  15

<210> SEQ ID NO 11
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 11

Ala Arg Ala Asp Ala Lys Ala Glu Ala Arg Ala Asp Ala Lys Ala Glu
1               5                   10                  15

<210> SEQ ID NO 12
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 12

Ala Lys Ala Glu Ala Arg Ala Asp Ala Lys Ala Glu Ala Arg Ala Asp
1               5                   10                  15

<210> SEQ ID NO 13
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 13

Ala Arg Ala Lys Ala Asp Ala Glu Ala Arg Ala Lys Ala Asp Ala Glu
1               5                   10                  15

<210> SEQ ID NO 14
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 14

Ala Lys Ala Arg Ala Glu Ala Asp Ala Lys Ala Arg Ala Asp Ala Glu
1               5                   10                  15
```

```
<210> SEQ ID NO 15
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 15

Ala Gln Ala Gln Ala Gln Ala Gln Ala Gln Ala Gln Ala Gln Ala Gln
1               5                   10                  15

<210> SEQ ID NO 16
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 16

Val Gln Val Gln Val Gln Val Gln Val Gln Val Gln Val Gln Val Gln
1               5                   10                  15

<210> SEQ ID NO 17
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 17

Tyr Gln Tyr Gln Tyr Gln Tyr Gln Tyr Gln Tyr Gln Tyr Gln Tyr Gln
1               5                   10                  15

<210> SEQ ID NO 18
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 18

His Gln His Gln His Gln His Gln His Gln His Gln His Gln His Gln
1               5                   10                  15

<210> SEQ ID NO 19
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 19

Ala Asn Ala Asn Ala Asn Ala Asn Ala Asn Ala Asn Ala Asn Ala Asn
1               5                   10                  15

<210> SEQ ID NO 20
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 20

Val Asn Val Asn Val Asn Val Asn Val Asn Val Asn Val Asn Val Asn
1               5                   10                  15

<210> SEQ ID NO 21
```

```
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 21

Tyr Asn Tyr Asn Tyr Asn Tyr Asn Tyr Asn Tyr Asn Tyr Asn Tyr Asn
1               5                   10                  15

<210> SEQ ID NO 22
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 22

His Asn His Asn His Asn His Asn His Asn His Asn His Asn His Asn
1               5                   10                  15

<210> SEQ ID NO 23
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 23

Ala Asn Ala Gln Ala Asn Ala Gln Ala Asn Ala Gln Ala Asn Ala Gln
1               5                   10                  15

<210> SEQ ID NO 24
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 24

Ala Gln Ala Asn Ala Gln Ala Asn Ala Gln Ala Asn Ala Gln Ala Asn
1               5                   10                  15

<210> SEQ ID NO 25
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 25

Val Asn Val Gln Val Asn Val Gln Val Asn Val Gln Val Asn Val Gln
1               5                   10                  15

<210> SEQ ID NO 26
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 26

Val Gln Val Asn Val Gln Val Asn Val Gln Val Asn Val Gln Val Asn
1               5                   10                  15

<210> SEQ ID NO 27
<211> LENGTH: 16
```

```
<212> TYPE: PRT
<213> ORGANISM: artificial
<220> FEATURE:
<223> OTHER INFORMATION: synthetic sequence designed for self assembly

<400> SEQUENCE: 27

Tyr Asn Tyr Gln Tyr Asn Tyr Gln Tyr Asn Tyr Gln Tyr Asn Tyr Gln
1               5                   10                  15

<210> SEQ ID NO 28
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 28

Tyr Gln Tyr Asn Tyr Gln Tyr Asn Tyr Gln Tyr Asn Tyr Gln Tyr Asn
1               5                   10                  15

<210> SEQ ID NO 29
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 29

His Asn His Gln His Asn His Gln His Asn His Gln His Asn His Gln
1               5                   10                  15

<210> SEQ ID NO 30
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 30

His Gln His Asn His Gln His Asn His Gln His Asn His Gln His Asn
1               5                   10                  15

<210> SEQ ID NO 31
<211> LENGTH: 18
<212> TYPE: PRT
<213> ORGANISM: artificial
<220> FEATURE:
<223> OTHER INFORMATION: synthetic sequence designed for self assembly

<400> SEQUENCE: 31

Ala Lys Ala Gln Ala Asp Ala Lys Ala Gln Ala Asp Ala Lys Ala Gln
1               5                   10                  15

Ala Asp

<210> SEQ ID NO 32
<211> LENGTH: 18
<212> TYPE: PRT
<213> ORGANISM: artificial
<220> FEATURE:
<223> OTHER INFORMATION: synthetic sequence designed for self assembly

<400> SEQUENCE: 32

Val Lys Val Gln Val Asp Val Lys Val Gln Val Asp Val Lys Val Gln
1               5                   10                  15

Val Asp
```

```
<210> SEQ ID NO 33
<211> LENGTH: 18
<212> TYPE: PRT
<213> ORGANISM: artificial
<220> FEATURE:
<223> OTHER INFORMATION: synthetic sequence designed for self assembly

<400> SEQUENCE: 33

Tyr Lys Tyr Gln Tyr Asp Tyr Lys Tyr Gln Tyr Asp Tyr Lys Tyr Gln
1               5                   10                  15

Tyr Asp

<210> SEQ ID NO 34
<211> LENGTH: 18
<212> TYPE: PRT
<213> ORGANISM: artificial
<220> FEATURE:
<223> OTHER INFORMATION: synthetic sequence designed for self assembly

<400> SEQUENCE: 34

His Lys His Gln His Asp His Lys His Gln His Asp His Lys His Gln
1               5                   10                  15

His Asp

<210> SEQ ID NO 35
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 35

Arg Ala Arg Ala Asp Ala Asp Ala Arg Ala Arg Ala Asp Ala Asp Ala
1               5                   10                  15

<210> SEQ ID NO 36
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 36

Arg Ala Asp Ala Arg Gly Asp Ala Arg Ala Asp Ala Arg Gly Asp Ala
1               5                   10                  15

<210> SEQ ID NO 37
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 37

Arg Ala Glu Ala Arg Ala Glu Ala Arg Ala Glu Ala Arg Ala Glu Ala
1               5                   10                  15

<210> SEQ ID NO 38
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 38
```

Lys Ala Asp Ala Lys Ala Asp Ala Lys Ala Asp Ala Lys Ala Asp Ala
1               5                   10                  15

<210> SEQ ID NO 39
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 39

Ala Glu Ala Glu Ala His Ala His Ala Glu Ala Glu Ala His Ala His
1               5                   10                  15

<210> SEQ ID NO 40
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 40

Phe Glu Phe Glu Phe Lys Phe Lys Phe Glu Phe Glu Phe Lys Phe Lys
1               5                   10                  15

<210> SEQ ID NO 41
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 41

Leu Glu Leu Glu Leu Lys Leu Lys Leu Glu Leu Glu Leu Lys Leu Lys
1               5                   10                  15

<210> SEQ ID NO 42
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 42

Ala Glu Ala Glu Ala Lys Ala Lys Ala Glu Ala Glu Ala Lys Ala Lys
1               5                   10                  15

<210> SEQ ID NO 43
<211> LENGTH: 12
<212> TYPE: PRT
<213> ORGANISM: artificial
<220> FEATURE:
<223> OTHER INFORMATION: synthetic sequence designed for self assembly

<400> SEQUENCE: 43

Ala Glu Ala Glu Ala Glu Ala Glu Ala Lys Ala Lys
1               5                   10

<210> SEQ ID NO 44
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 44

Lys Ala Lys Ala Lys Ala Lys Ala Glu Ala Glu Ala Glu Ala Glu Ala

```
                1               5                  10                 15

<210> SEQ ID NO 45
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 45

Ala Glu Ala Glu Ala Glu Ala Glu Ala Lys Ala Lys Ala Lys Ala Lys
1               5                  10                 15

<210> SEQ ID NO 46
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 46

Arg Ala Arg Ala Arg Ala Arg Ala Asp Ala Asp Ala Asp Ala Asp Ala
1               5                  10                 15

<210> SEQ ID NO 47
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 47

Ala Asp Ala Asp Ala Asp Ala Asp Ala Arg Ala Arg Ala Arg Ala Arg
1               5                  10                 15

<210> SEQ ID NO 48
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 48

Asp Ala Asp Ala Asp Ala Asp Ala Arg Ala Arg Ala Arg Ala Arg Ala
1               5                  10                 15

<210> SEQ ID NO 49
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 49

His Glu His Glu His Lys His Lys His Glu His Glu His Lys His Lys
1               5                  10                 15

<210> SEQ ID NO 50
<211> LENGTH: 20
<212> TYPE: PRT
<213> ORGANISM: artificial
<220> FEATURE:
<223> OTHER INFORMATION: synthetic sequence designed for self assembly

<400> SEQUENCE: 50

Val Glu Val Glu Val Glu Val Glu Val Glu Val Glu Val Glu Val Glu
1               5                  10                 15
```

```
Val Glu Val Glu
            20

<210> SEQ ID NO 51
<211> LENGTH: 20
<212> TYPE: PRT
<213> ORGANISM: artificial
<220> FEATURE:
<223> OTHER INFORMATION: synthetic sequence designed for self assembly

<400> SEQUENCE: 51

Arg Phe Arg Phe Arg Phe Arg Phe Arg Phe Arg Phe Arg Phe Arg Phe
1               5                   10                  15

Arg Phe Arg Phe
            20

<210> SEQ ID NO 52
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 52

Ala Lys Ala Lys Ala Glu Ala Glu
1               5

<210> SEQ ID NO 53
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 53

Arg Ala Arg Ala Asp Ala Asp Ala
1               5

<210> SEQ ID NO 54
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 54

Arg Ala Asp Ala Arg Ala Asp Ala
1               5

<210> SEQ ID NO 55
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 55

Ala Glu Ala Glu Ala Lys Ala Lys
1               5

<210> SEQ ID NO 56
<211> LENGTH: 4
<212> TYPE: PRT
<213> ORGANISM: artificial
<220> FEATURE:
<223> OTHER INFORMATION: synthetic sequence designed for self assembly
```

<400> SEQUENCE: 56

Lys Ala Glu Ala
1

<210> SEQ ID NO 57
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 57

Glu Ala Lys Ala
1

<210> SEQ ID NO 58
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 58

Lys Ala Glu Ala
1

<210> SEQ ID NO 59
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 59

Ala Glu Ala Lys
1

<210> SEQ ID NO 60
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 60

Ala Asp Ala Asp Ala Arg Ala Arg
1               5

<210> SEQ ID NO 61
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 61

Ala Arg Ala Asp
1

<210> SEQ ID NO 62
<211> LENGTH: 4
<212> TYPE: PRT
<213> ORGANISM: artificial
<220> FEATURE:
<223> OTHER INFORMATION: synthetic sequence designed for self assembly

```
<400> SEQUENCE: 62

Asp Ala Arg Ala
1

<210> SEQ ID NO 63
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 63

Arg Ala Asp Ala
1

<210> SEQ ID NO 64
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 64

Ala Asp Ala Arg
1

<210> SEQ ID NO 65
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 65

Ala Arg Ala Asp Ala Lys Ala Glu
1               5

<210> SEQ ID NO 66
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 66

Ala Lys Ala Glu Ala Arg Ala Asp
1               5

<210> SEQ ID NO 67
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 67

Ala Arg Ala Lys Ala Asp Ala Glu
1               5

<210> SEQ ID NO 68
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 68
```

```
Lys Ala Arg Ala Glu Ala Asp Ala
1               5
```

<210> SEQ ID NO 69
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 69

```
Ala Asn Ala Gln
1
```

<210> SEQ ID NO 70
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 70

```
Ala Gln Ala Asn
1
```

<210> SEQ ID NO 71
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 71

```
Val Asn Val Gln
1
```

<210> SEQ ID NO 72
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 72

```
Val Gln Val Asn
1
```

<210> SEQ ID NO 73
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 73

```
Tyr Asn Tyr Gln
1
```

<210> SEQ ID NO 74
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 74

Tyr Gln Tyr Asn
1

<210> SEQ ID NO 75
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 75

His Asn His Gln
1

<210> SEQ ID NO 76
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 76

His Gln His Asn
1

<210> SEQ ID NO 77
<211> LENGTH: 6
<212> TYPE: PRT
<213> ORGANISM: artificial
<220> FEATURE:
<223> OTHER INFORMATION: synthetic sequence designed for self assembly

<400> SEQUENCE: 77

Ala Lys Ala Gln Ala Asp
1               5

<210> SEQ ID NO 78
<211> LENGTH: 6
<212> TYPE: PRT
<213> ORGANISM: artificial
<220> FEATURE:
<223> OTHER INFORMATION: synthetic sequence designed for self assembly

<400> SEQUENCE: 78

Val Lys Val Gln Val Asp
1               5

<210> SEQ ID NO 79
<211> LENGTH: 6
<212> TYPE: PRT
<213> ORGANISM: artificial
<220> FEATURE:
<223> OTHER INFORMATION: synthetic sequence designed for self assembly

<400> SEQUENCE: 79

Tyr Lys Tyr Gln Tyr Asp
1               5

<210> SEQ ID NO 80
<211> LENGTH: 6
<212> TYPE: PRT
<213> ORGANISM: artificial
<220> FEATURE:
<223> OTHER INFORMATION: synthetic sequence designed for self assembly

<400> SEQUENCE: 80

His Lys His Gln His Asp

```
<210> SEQ ID NO 81
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 81

Arg Ala Asp Ala Arg Gly Asp Ala
1               5

<210> SEQ ID NO 82
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 82

Arg Ala Glu Ala
1

<210> SEQ ID NO 83
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 83

Lys Ala Asp Ala
1

<210> SEQ ID NO 84
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 84

Ala Glu Ala Glu Ala His Ala His
1               5

<210> SEQ ID NO 85
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 85

Phe Glu Phe Glu Phe Lys Phe Lys
1               5

<210> SEQ ID NO 86
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 86

Leu Glu Leu Glu Leu Lys Leu Lys
1               5
```

```
<210> SEQ ID NO 87
<211> LENGTH: 12
<212> TYPE: PRT
<213> ORGANISM: artificial
<220> FEATURE:
<223> OTHER INFORMATION: synthetic sequence designed for self assembly

<400> SEQUENCE: 87

Ala Glu Ala Glu Ala Glu Ala Glu Ala Lys Ala Lys
1               5                   10

<210> SEQ ID NO 88
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 88

His Glu His Glu His Lys His Lys
1               5

<210> SEQ ID NO 89
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 89

Ala Arg Ala Arg Ala Asp Ala Asp
1               5
22
```